United States Patent
Sakamoto et al.

(10) Patent No.: US 6,406,898 B1
(45) Date of Patent: *Jun. 18, 2002

(54) D-PANTOLACTONE HYDROLASE AND GENE ENCODING THE SAME

(75) Inventors: Keiji Sakamoto, Takaoka; Hideaki Yamada, Kyoto; Sakayu Shimizu, Kyoto; Michihiko Kobayashi, Kyoto, all of (JP)

(73) Assignee: Daiichi Fine Chemical Co., Ltd., Takaoka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,047

(22) PCT Filed: Sep. 13, 1996

(86) PCT No.: PCT/JP96/02620

§ 371 (c)(1),
(2), (4) Date: Sep. 19, 1997

(87) PCT Pub. No.: WO97/10341

PCT Pub. Date: Mar. 20, 1997

(30) Foreign Application Priority Data

Sep. 13, 1995 (JP) .............................. 7-259451

(51) Int. Cl.[7] .............................. C12N 9/14; C12N 1/00; C12N 1/14; C07H 21/04

(52) U.S. Cl. .................... 435/195; 435/325; 435/243; 435/254.1; 435/254.7; 536/23.2

(58) Field of Search ................................ 435/195, 325, 435/243, 254.1, 254.7; 536/23.2

(56) References Cited

U.S. PATENT DOCUMENTS

| 5,275,949 A | 1/1994 | Sakamoto et al. ........... 435/280 |
| 5,372,940 A * | 12/1994 | Sakamoto et al. ........... 435/195 |

FOREIGN PATENT DOCUMENTS

| EP | 0 436 730 | 7/1991 |
| EP | 0 504 421 | 9/1992 |
| JP | 4-144681 | 5/1992 |
| WO | 92/06182 | 4/1992 |

OTHER PUBLICATIONS

Fontana, A. et al., in Practical Protein Chemistry—A Handbook, A. Darbre, ed., pp. 67–120, 1986.*
Lee, C. et al., Science, vol. 239, pp. 1288–1291, Mar. 1988.*
Amann, E. et al., Gene, vol. 69, pp. 301–315, Mar. 1988.*
Alberts, et al., The Molecular Biology of the Cell, 3$^{rd}$ Edition, pp. 608–609 and p. 455 (1995), abstract attached.
Sambrook, et al., "Molecular Cloning", A Laboratory Manual, 2$^{nd}$ Edition, Cold Spring Harbor Laboratory Press, p. 16.3 (1989).
Wiley, et al., Practical Protein Chemistry—A Handbook, A Wiley—Interscience Publication, pp. 68–120 (1986).

* cited by examiner

Primary Examiner—Ponnathapu Achutamurthy
Assistant Examiner—Yong Pak
(74) Attorney, Agent, or Firm—Foley & Lardner

(57) ABSTRACT

A novel enzyme which is useful in the optical resolution of D,L-pantolactone via D-selective asymmetric hydrolysis and a gene encoding the the same are provided. The invention discloses the gene coding for a natural D-pantolactone hydrolase (for example, one originating in *Fusarium oxysporum*) or proteins having an activity substantially equivalent thereto; host cells transformed with DNA containing a nucleotide sequence coding for said protein, processes for producing said protein via using said host cells and uses of said proteins and host cells.

2 Claims, 5 Drawing Sheets

| Peptide Number | Amino Acid Sequence |
|---|---|
| N-terminal | A K L P S T A Q I I D Q K S F N V L K D V P P P A V A ★ D S |
| No.1 | Q D E V K |
| No.2 | E A D A V R K |
| No.3 | L I G K |
| No.4 | L Y D |
| No.5 | S S I I Q K |
| No.6 | I S L K |
| No.7 | G R M I X T G Q T K |
| No.8 | L P S T A Q I I D Q K |
| No.9 | S F N V L K |
| No.10 | V T V V D S N P Q V I N P N G G T Y Y K |
| No.11 | G R V Y A G X G D G V H V W N P S G K |
| No.12 | I Y T G T V A A N F Q F A G K |
| No.13 | L F Y V T L G A S G P K |
| No.14 | T F A Y V A S F I P D G V H T D S K |
| No.15 | P F H V Y D E E F Y D V I G K |
| No.16 | V Y V T D T G I A L G F Y G R ★ L S S P A S V Y S F D V N Q D G T L Q N R K |
| No.17 | D V P P P A V A ★ D S L V F T (W) P G V T E E S L V E K |
| No.18 | D P S L T L I A T S D T D P I F H E A V V W Y P P T E(E)V F F V Q N A G A P A A G T G L ★ K |
| No.19 | G N I I F A G E G Q G D D V P S A L Y L M N P L P(P)Y ★ T T T L X ---- |

★ : N residne glycosylated    X : Uncertain residne

| Peptide Number | Amino Acid Sequence |
|---|---|
| N-terminal | A K L P S T A Q I I D Q K S F N V L K D V P P P A V A ★ D S |
| No.1 | Q D E V K |
| No.2 | E A D A V R K |
| No.3 | L I G K |
| No.4 | L Y D |
| No.5 | S S I I Q K |
| No.6 | I S L K |
| No.7 | G R M I X T G Q T K |
| No.8 | L P S T A Q I I D Q K |
| No.9 | S F N V L K |
| No.10 | V T V V D S N P Q V I N P N G G T Y Y K |
| No.11 | G R V Y A G X G D G V H V W N P S G K |
| No.12 | I Y T G T V A A N F Q F A G K |
| No.13 | L F Y V T L G A S G P K |
| No.14 | T F A Y V A S F I P D G V H T D S K |
| No.15 | P F H V Y D E E F Y D V I G K |
| No.16 | V Y V T D T G I A L G F Y G R ★ L S S P A S V Y S F D V N Q D G T L Q N R K |
| No.17 | D V P P P A V A ★ D S L V F T (W) P G V T E E S L V E K |
| No.18 | D P S L T L I A T S D T D P I F H E A V V W Y P P T E (E) V F F V Q N A G A P A A G T G L ★ K |
| No.19 | G N I I F A G E G Q G D D V P S A L Y L M N P L P (P) Y ★ T T T L X ---- |

★ : N residne glycosylated  X : Uncertain residne

FIG. 1

```
         10                20                30                40                50
AK L PSTAQII DQK SFNVLK D VPPPAVANDS LVFTWPGVTE ESLVEK PFHV
  No.8            No.9       No.17                              No.15
         60                70                80                90               100
YDEEFYDVIG K DPSLTLIAT SDTDPIFHEA VVWYPPTEEV FFVQNAGAPA
              No.18
        110               120               130               140               150
AGTGLNK SSI IQK ISLK EAD AVRK GK QDEV K VTVVDSNPQ VINPNGGTYY
         No.5   No.6 No.2              No.1  No.10
        160               170               180               190               200
K GNIIFAGEG QGDDVPSALY LMNPLPPYNT TLLLNNYFGR QFNSLNDVGI
 No.19
        210               220               230               240               250
NPRNGDLYFT DTLYGYLQDF RPVPGLRNQV YRYNFDTGAV TVVADDFTLP
        260               270               280               290               300
NGIGFGPDGK K VYVTDTGIA LGFYGRNLSS PASVYSFDVN QDGTLQNRK T
              No.16
        310               320               330               340               350
FAYVASFIPD GVHTDSK GRV YAGCGDGVHV WNPSGK LIGK IYTGTVAANF
 No.14              No.11                          No.3      No.12
        360               370               380
QFAGK GRMII TGQTK LFYVT LGASGPK LYD
 No.7            No.13                No.4
```

FIG. 2

Sense primer (N-terminal sequence)

```
     Phe His Val Tyr Asp Glu Glu Phe Tyr Asp
5'  AAAGC TTC CAC GTC TAC GAC GAA GAA TTC TAC GAC GT  3'
    HindIII  T              T   T   G   G   T   T   T
```

Antisense primer (Internal sequence)

```
     Pro Asn Trp Val His Val Gly Asp
5'  GGCTTGCTGCA GGG GTT CCA AAC GTG AAC ACC GTC  3'
     PstI       A       C   A   C   C   A
                        G       G   G
                                T   T   T
```

FIG. 3

FL-E1 (Sense primer)

```
                   SD                    MetAlaLysLeuProSerThrAlaGln
5' GTGAATTCTAAGGAGGAATAGGTGATGGCTAAGCTTCCTTCTACGGCTCAG 3'
   EcoRI                Stop Start
```

FL-E2 (Antisense primer)

```
5' GTAAGTCTAGAGAAGTGAACATTTCTAATCATAGAG 3'
        XbaI
```

FIG. 4

```
         10         20         30         40         50         60
CCATGGTGGCTGCTAAGCTTCCTTCTACGGCTCAGATTATTGATCAGAAGTCGTTCAATG
     A   K   L   P   S   T   A   Q   I   I   D   Q   K   S   F   N   V
         70         80         90        100        110        120
TCTTGAAGGATGTGCCACCTCCTGCAGTGGCCAATGACTCTCTGGTGTTCACTTGGCCTG
  L   K   D   V   P   P   P   A   V   A   N   D   S   L   V   F   T   W   P   G
        130        140        150        160        170        180
GTGTAACTGAGGAGTCTCTTGTTGAGAAGCCTTTCCATGTCTACGATGAAGAGTTTTACG
   V   T   E   E   S   L   V   E   K   P   F   H   V   Y   D   E   E   F   Y   D
        190        200        210        220        230        240
ATGTAATTGGAAAAGACCCCTCTTTGACCCTCATCGCAACATCGGACACCGACCCAATCT
    V   I   G   K   D   P   S   L   T   L   I   A   T   S   D   T   D   P   I   F
        250        260        270        280        290        300
TCCATGAGGCTGTCGTATGGTATCCTCCTACTGAAGAGGTGTTCTTTGTGCAGAATGCTG
  H   E   A   V   V   W   Y   P   P   T   E   E   V   F   F   V   Q   N   A   G
        310        320        330        340        350        360
GCGCTCCTGCCGCAGGCACTGGCTTGAACAAGTCTTCCATCATTCAGAAGATTTCCCTCA
   A   P   A   A   G   T   G   L   N   K   S   S   I   I   Q   K   I   S   L   K
        370        380        390        400        410        420
AGGAGGCCGATGCTGTTCGCAAGGGCAAGCAGGATGAGGTCAAGGTCACAGTTGTTGACT
   E   A   D   A   V   R   K   G   K   Q   D   E   V   K   V   T   V   V   D   S
        430        440        450        460        470        480
CGAACCCTCAGGTTATCAACCCAAATGGTGGTACTTACTACAAGGGCAACATCATCTTCG
   N   P   Q   V   I   N   P   N   G   G   T   Y   Y   K   G   N   I   I   F   A
        490        500        510        520        530        540
CTGGTGAGGGCCAAGGCGACGATGTTCCCTCTGCGCTGTACCTCATGAACCCTCTCCCTC
   G   E   G   Q   G   D   D   V   P   S   A   L   Y   L   M   N   P   L   P   P
        550        560        570        580        590        600
CTTACAACACCACCACCCTTCTCAACAACTACTTCGGTCGCCAGTTCAACTCCCTCAACG
   Y   N   T   T   T   L   L   N   N   Y   F   G   R   Q   F   N   S   L   N   D
        610        620        630        640        650        660
ACGTCGGTATCAACCCCAGGAACGGTGACCTGTACTTCACCGATACCCTCTACGGATATC
   V   G   I   N   P   R   N   G   D   L   Y   F   T   D   T   L   Y   G   Y   L
        670        680        690        700        710        720
TCCAAGACTTCCGTCCTGTTCCTGGTCTGCGAAACCAGGTCTATCGTTACAACTTTGACA
  Q   D   F   R   P   V   P   G   L   R   N   Q   V   Y   R   Y   N   F   D   T
        730        740        750        760        770        780
CTGGCGCTGTCACTGTTGTCGCTGATGACTTTACCCTTCCCAACGGTATTGGCTTTGGCC
   G   A   V   T   V   V   A   D   D   F   T   L   P   N   G   I   G   F   G   P
        790        800        810        820        830        840
CCGACGGCAAGAAGGTTTATGTCACCGACACTGGCATCGCTCTCGGTTTCTACGGTCGCA
   D   G   K   K   V   Y   V   T   D   T   G   I   A   L   G   F   Y   G   R   N
        850        860        870        880        890        900
ACCTCTCTTCTCCCGCTTCTGTTTACTCTTTCGACGTGAACCAGGACGGTACTCTTCAGA
   L   S   S   P   A   S   V   Y   S   F   D   V   N   Q   D   G   T   L   Q   N
        910        920        930        940        950        960
ACCGCAAGACCTTTGCTTATGTTGCCTCATTCATCCCCGATGGTGTCCACACTGACTCCA
   R   K   T   F   A   Y   V   A   S   F   I   P   D   G   V   H   T   D   S   K
        970        980        990       1000       1010       1020
AGGGTCGTGTTTATGCTGGCTGCGGTGATGGTGTCCATGTCTGGAACCCCTCTGGCAAGC
   G   R   V   Y   A   G   C   G   D   G   V   H   V   W   N   P   S   G   K   L
       1030       1040       1050       1060       1070       1080
TCATCGGCAAGATCTACACCGGAACGGTTGCTGCTAACTTCCAGTTTGCTGGTAAGGGAA
  I   G   K   I   Y   T   G   T   V   A   A   N   F   Q   F   A   G   K   G   R
       1090       1100       1110       1120       1130       1140
GGATGATAATTACTGGACAGACGAAGTTGTTCTATGTCACTCTAGGGGCTTCGGGTCCCA
   M   I   I   T   G   Q   T   K   L   F   Y   V   T   L   G   A   S   G   P   K
       1150       1160       1170       1180       1190       1200
AGCTCTATGATTAGAAATGTTCACTTCTCTATACTTACATAGATAATACATGGCATTTGA
   L   Y   D   *
       1210       1220       1230
CTTTTGAAAAAAAAAAAAAAAAAAACCATGG
```

FIG. 5

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:1:

```
Ala Lys Leu Pro Ser Thr Ala Gln Ile Ile A sp Gln Lys Ser Phe Asn
 1               5                  10                  15

Val Leu Lys Asp Val Pro Pro Ala Val A la Asn Asp Ser Leu Val
                20                  25                  30

Phe Thr Trp Pro Gly Val Thr Glu Glu Ser L eu Val Glu Lys Pro Phe
            35                  40                  45

His Val Tyr Asp Glu Glu Phe Tyr Asp Val I le Gly Lys Asp Pro Ser
        50                  55                  60

Leu Thr Leu Ile Ala Thr Ser Asp Thr Asp P ro Ile Phe His Glu Ala
65                  70                  75                  80
```

-continued

```
Val Val Trp Tyr Pro Pro Thr Glu Glu Val Phe Phe Val Gln Asn Ala
                85                  90                  95
Gly Ala Pro Ala Ala Gly Thr Gly Leu Asn Lys Ser Ser Ile Ile Gln
            100                 105                 110
Lys Ile Ser Leu Lys Glu Ala Asp Ala Val Arg Lys Gly Lys Gln Asp
        115                 120                 125
Glu Val Lys Val Thr Val Val Asp Ser Asn Pro Gln Val Ile Asn Pro
130                 135                 140
Asn Gly Gly Thr Tyr Tyr Lys Gly Asn Ile Ile Phe Ala Gly Glu Gly
145                 150                 155                 160
Gln Gly Asp Asp Val Pro Ser Ala Leu Tyr Leu Met Asn Pro Leu Pro
                165                 170                 175
Pro Tyr Asn Thr Thr Thr Leu Leu Asn Asn Tyr Phe Gly Arg Gln Phe
            180                 185                 190
Asn Ser Leu Asn Asp Val Gly Ile Asn Pro Arg Asn Gly Asp Leu Tyr
        195                 200                 205
Phe Thr Asp Thr Leu Tyr Gly Tyr Leu Gln Asp Phe Arg Pro Val Pro
210                 215                 220
Gly Leu Arg Asn Gln Val Tyr Arg Tyr Asn Phe Asp Thr Gly Ala Val
225                 230                 235                 240
Thr Val Val Ala Asp Asp Phe Thr Leu Pro Asn Gly Ile Gly Phe Gly
                245                 250                 255
Pro Asp Gly Lys Lys Val Tyr Val Thr Asp Thr Gly Ile Ala Leu Gly
            260                 265                 270
Phe Tyr Gly Arg Asn Leu Ser Ser Pro Ala Ser Val Tyr Ser Phe Asp
        275                 280                 285
Val Asn Gln Asp Gly Thr Leu Gln Asn Arg Lys Thr Phe Ala Tyr Val
290                 295                 300
Ala Ser Phe Ile Pro Asp Gly Val His Thr Asp Ser Lys Gly Arg Val
305                 310                 315                 320
Tyr Ala Gly Cys Gly Asp Gly Val His Val Trp Asn Pro Ser Gly Lys
                325                 330                 335
Leu Ile Gly Lys Ile Tyr Thr Gly Thr Val Ala Ala Asn Phe Gln Phe
            340                 345                 350
Ala Gly Lys Gly Arg Met Ile Ile Thr Gly Gln Thr Lys Leu Phe Tyr
        355                 360                 365
Val Thr Leu Gly Ala Ser Gly Pro Lys Leu Tyr Asp
370                 375                 380
```

(2) INFORMATION FOR SEQ ID NO:2:

(i) SEQUENCE CHARACTERISTICS:
        (A) LENGTH: 1229 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Fusarium oxysporum IFO 5942

(ix) FEATURE:
        (A) NAME/KEY: CDS
        (B) LOCATION: 12..1151

(xi) SEQUENCE DESCRIPTION: SEQ ID NO:2:

```
CCATGGTGGC T GCT AAG CTT CCT TCT ACG GCT CAG  ATT ATT GAT CAG AAG     50
           Ala Lys Leu Pro Ser Thr Ala Gln  Ile Ile Asp Gln Lys
```

```
            1               5                    10
TCG TTC AAT GTC TTG AAG GAT GTG CCA CCT C CT GCA GTG GCC AAT GAC      98
Ser Phe Asn Val Leu Lys Asp Val Pro Pro P ro Ala Val Ala Asn Asp
     15                  20                    25

TCT CTG GTG TTC ACT TGG CCT GGT GTA ACT G AG GAG TCT CTT GTT GAG     146
Ser Leu Val Phe Thr Trp Pro Gly Val Thr G lu Glu Ser Leu Val Glu
 30                  35                    40                  45

AAG CCT TTC CAT GTC TAC GAT GAA GAG TTT T AC GAT GTA ATT GGA AAA     194
Lys Pro Phe His Val Tyr Asp Glu Glu Phe T yr Asp Val Ile Gly Lys
                 50                    55                  60

GAC CCC TCT TTG ACC CTC ATC GCA ACA TCG G AC ACC GAC CCA ATC TTC     242
Asp Pro Ser Leu Thr Leu Ile Ala Thr Ser A sp Thr Asp Pro Ile Phe
             65                    70                  75

CAT GAG GCT GTC GTA TGG TAT CCT CCT ACT G AA GAG GTG TTC TTT GTG     290
His Glu Ala Val Val Trp Tyr Pro Pro Thr G lu Glu Val Phe Phe Val
         80                    85                  90

CAG AAT GCT GGC GCT CCT GCC GCA GGC ACT G GC TTG AAC AAG TCT TCC     338
Gln Asn Ala Gly Ala Pro Ala Ala Gly Thr G ly Leu Asn Lys Ser Ser
     95                  100                   105

ATC ATT CAG AAG ATT TCC CTC AAG GAG GCC G AT GCT GTT CGC AAG GGC     386
Ile Ile Gln Lys Ile Ser Leu Lys Glu Ala A sp Ala Val Arg Lys Gly
110                 115                   120                 125

AAG CAG GAT GAG GTC AAG GTC ACA GTT GTT G AC TCG AAC CCT CAG GTT     434
Lys Gln Asp Glu Val Lys Val Thr Val Val A sp Ser Asn Pro Gln Val
                130                   135                 140

ATC AAC CCA AAT GGT GGT ACT TAC TAC AAG G GC AAC ATC ATC TTC GCT     482
Ile Asn Pro Asn Gly Gly Thr Tyr Tyr Lys G ly Asn Ile Ile Phe Ala
            145                   150                 155

GGT GAG GGC CAA GGC GAC GAT GTT CCC TCT G CG CTG TAC CTC ATG AAC     530
Gly Glu Gly Gln Gly Asp Asp Val Pro Ser A la Leu Tyr Leu Met Asn
        160                   165                 170

CCT CTC CCT CCT TAC AAC ACC ACC ACC CTT C TC AAC AAC TAC TTC GGT     578
Pro Leu Pro Pro Tyr Asn Thr Thr Thr Leu L eu Asn Asn Tyr Phe Gly
    175                   180                 185

CGC CAG TTC AAC TCC CTC AAC GAC GTC GGT A TC AAC CCC AGG AAC GGT     626
Arg Gln Phe Asn Ser Leu Asn Asp Val Gly I le Asn Pro Arg Asn Gly
190                   195                 200                 205

GAC CTG TAC TTC ACC GAT ACC CTC TAC GGA T AT CTC CAA GAC TTC CGT     674
Asp Leu Tyr Phe Thr Asp Thr Leu Tyr Gly T yr Leu Gln Asp Phe Arg
                  210                 215                 220

CCT GTT CCT GGT CTG CGA AAC CAG GTC TAT C GT TAC AAC TTT GAC ACT     722
Pro Val Pro Gly Leu Arg Asn Gln Val Tyr A rg Tyr Asn Phe Asp Thr
              225                 230                 235

GGC GCT GTC ACT GTT GTC GCT GAT GAC TTT A CC CTT CCC AAC GGT ATT     770
Gly Ala Val Thr Val Val Ala Asp Asp Phe T hr Leu Pro Asn Gly Ile
          240                 245                 250

GGC TTT GGC CCC GAC GGC AAG AAG GTT TAT G TC ACC GAC ACT GGC ATC     818
Gly Phe Gly Pro Asp Gly Lys Lys Val Tyr V al Thr Asp Thr Gly Ile
      255                 260                 265

GCT CTC GGT TTC TAC GGT CGC AAC CTC TCT T CT CCC GCT TCT GTT TAC     866
Ala Leu Gly Phe Tyr Gly Arg Asn Leu Ser S er Pro Ala Ser Val Tyr
270                 275                 280                 285

TCT TTC GAC GTG AAC CAG GAC GGT ACT CTT C AG AAC CGC AAG ACC TTT     914
Ser Phe Asp Val Asn Gln Asp Gly Thr Leu G ln Asn Arg Lys Thr Phe
                290                 295                 300

GCT TAT GTT GCC TCA TTC ATC CCC GAT GGT G TC CAC ACT GAC TCC AAG     962
Ala Tyr Val Ala Ser Phe Ile Pro Asp Gly V al His Thr Asp Ser Lys
            305                 310                 315

GGT CGT GTT TAT GCT GGC TGC GGT GAT GGT G TC CAT GTC TGG AAC CCC    1010
```

```
Gly Arg Val Tyr Ala Gly Cys Gly Asp Gly Val His Val Trp Asn Pro
            320                 325                 330

TCT GGC AAG CTC ATC GGC AAG ATC TAC ACC GGA ACG GTT GCT GCT AAC      1058
Ser Gly Lys Leu Ile Gly Lys Ile Tyr Thr Gly Thr Val Ala Ala Asn
    335                 340                 345

TTC CAG TTT GCT GGT AAG GGA AGG ATG ATA ATT ACT GGA CAG ACG AAG      1106
Phe Gln Phe Ala Gly Lys Gly Arg Met Ile Ile Thr Gly Gln Thr Lys
350                 355                 360                 365

TTG TTC TAT GTC ACT CTA GGG GCT TCG GGT CCC AAG CTC TAT GAT          1151
Leu Phe Tyr Val Thr Leu Gly Ala Ser Gly Pro Lys Leu Tyr Asp
                370                 375                 380

TAGAAATGTT CACTTCTCTA TACTTACATA GATAATACAT GGCATTTGAC T TTTGAAAAA   1211

AAAAAAAAAA AACCATGG                                                  1229

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-si te
        (B) LOCATION: 28
        (D) OTHER INFORMATION: /product= "glycosylated Asn"

(xi) SEQUENCE DESCRIPTION: SEQ ID NO:3:

Ala Lys Leu Pro Ser Thr Ala Gln Ile Ile Asp Gln Lys Ser Phe Asn
1               5                   10                  15

Val Leu Lys Asp Val Pro Pro Ala Val Ala Asn Asp Ser
            20                  25                  30

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Gln Asp Glu Val Lys
1               5

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Glu Ala Asp Ala Val Arg Lys
1               5

(2) INFORMATION FOR SEQ ID NO:6:

(i) SEQUENCE CHARACTERISTICS:
```

```
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Leu Ile Gly Lys
1

(2) INFORMATION FOR SEQ ID NO:7:

(i) SEQUENCE CHARACTERISTICS:
            (A) LENGTH: 3 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Leu Tyr Asp
1

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Ser Ser Ile Ile Gln Lys
1               5

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Ile Ser Leu Lys
1

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Gly Arg Met Ile Xaa Thr Gly Gln Thr Lys
1               5                   10

(2) INFORMATION FOR SEQ ID NO:11:
```

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:11:

Leu Pro Ser Thr Ala Gln Ile Ile Asp Gln Lys
1               5                   10

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Ser Phe Asn Val Leu Lys
1               5

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Val Thr Val Val Asp Ser Asn Pro Gln Val Ile Asn Pro Asn Gly Gly
1               5                   10                  15

Thr Tyr Tyr Lys
            20

(2) INFORMATION FOR SEQ ID NO:14:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Gly Arg Val Tyr Ala Gly Xaa Gly Asp Gly Val His Val Trp Asn Pro
1               5                   10                  15

Ser Gly Lys (2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Ile Tyr Thr Gly Thr Val Ala Ala Asn Phe Gln Phe Ala Gly Lys
1               5                   10                  15
```

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Leu Phe Tyr Val Thr Leu Gly Ala Ser Gly Pro Lys
1               5                   10
```

(2) INFORMATION FOR SEQ ID NO:17:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Thr Phe Ala Tyr Val Ala Ser Phe Ile Pro Asp Gly Val His Thr Asp
1               5                   10                  15
Ser Lys
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Pro Phe His Val Tyr Asp Glu Glu Phe Tyr Asp Val Ile Gly Lys
1               5                   10                  15
```

(2) INFORMATION FOR SEQ ID NO:19:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 16
        (D) OTHER INFORMATION: /product= "glycosylated Asn"

(xi) SEQUENCE DESCRIPTION: SEQ ID NO:19:

```
Val Tyr Val Thr Asp Thr Gly Ile Ala Leu Gly Phe Tyr Gly Arg Asn
1               5                   10                  15
Leu Ser Ser Pro Ala Ser Val Tyr Ser Phe Asp Val Asn Gln Asp Gly
                20                  25                  30
Thr Leu Gln Asn Arg Lys
                35
```

(2) INFORMATION FOR SEQ ID NO:20:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-si te
        (B) LOCATION: 9
        (D) OTHER INFORMATION: /product= "glycosylated Asn"

(xi) SEQUENCE DESCRIPTION: SEQ ID NO:20:

```
Asp Val Pro Pro Pro Ala Val Ala Asn Asp S er Leu Val Phe Thr Trp
1               5                  10                  15
Pro Gly Val Thr Glu Glu Ser Leu Val Glu L ys
            20                  25
```

(2) INFORMATION FOR SEQ ID NO:21:

(i) SEQUENCE CHARACTERISTICS:
        (A) LENGTH: 46 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-si te
        (B) LOCATION: 45
        (D) OTHER INFORMATION: /product= "glycosylated Asn"

(xi) SEQUENCE DESCRIPTION: SEQ ID NO:21:

```
Asp Pro Ser Leu Thr Leu Ile Ala Thr Ser A sp Thr Asp Pro Ile Phe
1               5                  10                  15
His Glu Ala Val Val Trp Tyr Pro Pro Thr G lu Glu Val Phe Phe Val
            20                  25                  30
Gln Asn Ala Gly Ala Pro Ala Ala Gly Thr G ly Leu Asn Lys
        35                  40                  45
```

(2) INFORMATION FOR SEQ ID NO:22:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-si te
        (B) LOCATION: 28
        (D) OTHER INFORMATION: /product= "glycosylated Asn"

(xi) SEQUENCE DESCRIPTION: SEQ ID NO:22:

```
Gly Asn Ile Ile Phe Ala Gly Glu Gly Gln G ly Asp Asp Val Pro Ser
1               5                  10                  15
Ala Leu Tyr Leu Met Asn Pro Leu Pro Pro T yr Asn Thr Thr Thr Leu
            20                  25                  30
Xaa
```

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: CDS
        (B) LOCATION: 7..36

(xi) SEQUENCE DESCRIPTION: SEQ ID NO:23:

```
AAAAGC TTY CAC GTC TAY GAY GAR GAR TTY TAY GAY GT           38
       Phe His Val Tyr Asp Glu G lu Phe Tyr Asp
        1           5                       10
```

(2) INFORMATION FOR SEQ ID NO:24:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:24:

```
Phe His Val Tyr Asp Glu Glu Phe Tyr Asp
 1           5                       10
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

```
Pro Asn Trp Val His Val Gly Asp
 1           5
```

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO:26:

```
GGCTTGCTGC AGGGRTTCCA NACRTGNACN CCRTC                      35
```

(2) INFORMATION FOR SEQ ID NO:27:

(i) SEQUENCE CHARACTERISTICS:
        (A) LENGTH: 51 base pairs
        (B) TYPE: nucleic acid
        (C) STRANDEDNESS: single
        (D) TOPOLOGY: linear -continued

```
        (ii) MOLECULE TYPE: other nucleic acid
             (A) DESCRIPTION: /desc = "primer"

(ix) FEATURE:
             (A) NAME/KEY: CDS
             (B) LOCATION: 25..51

(xi) SEQUENCE DESCRIPTION: SEQ ID NO:27:

GTGAATTCTA AGGAGGAATA GGTG ATG GCT AAG CTT CCT TCT ACG GCT CAG            51
                          Met Ala Lys Leu Pro Ser Thr Ala Gln
                            1               5

(2) INFORMATION FOR SEQ ID NO:28:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:28:

Met Ala Lys Leu Pro Ser Thr Ala Gln
  1               5

(2) INFORMATION FOR SEQ ID NO:29:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
             (A) DESCRIPTION: /desc = "primer"

(iv) ANTI-SENSE: YES (xi) SEQUENCE DESCRIPTION: SEQ ID NO:29:

GTAAGTCTAG AGAAGTGAAC ATTTCTAATC ATAGAG                                   36
```

D-PANTOLACTONE HYDROLASE AND GENE ENCODING THE SAME

TECHNICAL FIELD

The present invention relates to a novel enzyme which is useful for an optical resolution of D,L-pantolactone through a D-selective asymmetric hydrolysis process and also to a gene encoding the same. More particularly, the present invention relates to proteins having a natural D-pantolactone hydrolase activity, produced by *Fusarium oxysporum*, or an activity substantially equivalent to the same and genes coding for the same. Specifically, the present invention relates to DNA containing a nucleotide sequence coding for said protein; to host cells transformed or transfected with said DNA; to a process for the production of said D-pantolactone hydrolase protein via using said host cells; and to the use of such proteins and host cells.

BACKGROUND ART

D-Pantolactone has been known as an intermediate in the preparation of D-pantothenic acid and pantethine which are useful as vitamins of medical or physiological importance. D-Pantolactone has heretofore been prepared through an optical resolution of a chemically-synthesized D,L-pantolactone. Such a process, however, has disadvantages in that it requires the use of expensive optical resolving agents such as quinine or brucine and further that the recovery of D-pantolactone is not easy. In order to solve such problems, the present inventors already proposed an optical resolving method by an enzymatic asymmetric hydrolysis of D,L-pantolactone in Unexamined Japanese Patent Publication (KOKAI TOKKYO) Nos. Hei 03-65,198 and Hei 04-144,681.

Thus, it is a process for the production of D-pantolactone, wherein the D-pantolactone in D,L-pantolactone mixtures is selectively subjected to an asymmetric hydrolysis using a microorganism possessing a lactone-hydrolyzing activity to form D-pantoic acid, which is then separated and converted into D-pantolactone, wherein said microorganism is a member selected from the group consisting of microorganisms belonging to the genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma. It is also a process for producing D-pantolactone hydrolase which comprises using a microorganism belonging to the above-mentioned genus.

However, it cannot be always said that many of those microorganisms disclosed as above possess a hydrolyzing activity to such an extent that they are immediately applicable in industry. Furthermore, in increasing the enzymatic activity of said microorganisms to an industrially applicable level, troublesome and difficult investigations requiring long time are needed for establishing conditions for growth of cells, conditions for enzyme activity induction, etc. There is another problem that, since said microorganisms are true fungus, their cell bodies are in variously shaped hyphae and, as compared with bacteria having a single-shape, it is considerably difficult to prepare immobilized cells which are advantageous for industrial production. There is still another problem that, in purifying the enzyme from the cells, its recovery rate is considerably poor so far as D-pantolactone hydrolase is concerned.

DISCLOSURE OF THE INVENTION

An object of the present invention is to solve those problems and also to provide means for making a significant increase of the enzymatic activity possible, for example, means for modifying and improving the D-pantolactone hydrolase per se.

Thus, one aspect of the present invention is to disclose and provide a novel gene which codes for a protein having either a naturally-occurring D-pantolactone hydrolase activity (such as a *Fusarium oxysporum* D-pantolactone hydrolase activity) or an activity substantially equivalent thereto; a host cell transformed with DNA containing a nucleotide sequence coding for said protein; a process for producing said protein via using said host cell; and uses of said proteins and host cells.

The present invention directed to a gene coding for D-pantolactone hydrolase isolated from the above-mentioned microorganisms possessing the ability to hydrolyze a lactone and a system, with a high efficiency and rich productivity, for producing D-pantolactone is successfully developed through utilizing the D-pantolactone hydrolase gene isolated as such, not only solves the above-mentioned various problems but also greatly contributes to the development of enzymes possessing the ability to hydrolyze a lactone, together with new functions; and to the development of techniques using the novel enzyme. Particularly, the present inventors have succeeded in isolating a novel gene coding for a hydrolase with a D-pantolactone hydrolyzing ability, derived from microorganisms of the genus Fusarium (such as *Fusarium oxysporum*) which produces the D-pantolactone hydrolase, whereby the present invention has been achieved.

The present invention relates to:

(i) a protein having a natural D-pantolactone hydrolase activity or an activity substantially equivalent thereto or a salt thereof; or (ii) a protein having a primary structural conformation substantially equivalent thereto or a salt thereof;

(iii) a characteristic partial peptide of said protein or a salt thereof;

(iv) genes, such as DNA and RNA, coding for said protein;

(v) vectors or plasmids, containing said gene operably in a gene recombination technique;

(vi) host cells transformed with such a vector, etc.;

(vii) a process for producing said protein or a salt thereof which comprises culturing said host cell;

(viii) a process for producing D-pantolactone which comprises an optical resolution of D,L-pantolactone with such a gene-manipulated host cell (transformant), such a recombinant protein or a salt thereof, etc.; and (ix) a system means, such as an immobilized enzyme, for producing D-pantolactone.

In the present invention, a preferred recombinant protein is a D-pantolactone hydrolase having an amino acid sequence of SEQ ID NO:1 or an amino acid sequence substantially equivalent thereto, or a salt thereof.

Accordingly, one aspect of the present invention is:

(1) a protein having a naturally-occurring D-pantolactone hydrolase activity or an activity substantially equivalent thereto or having a primary structural conformation substantially equivalent thereto, or a salt thereof;

(2) the protein according to the above (1), wherein said protein having a naturally-occurring D-pantolactone hydrolase activity is originating in a microorganism belonging to a member selected from the group consisting of genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma;

(3) the protein according to the above (1), wherein said protein having a naturally-occurring D-pantolactone hydrolase activity is originating in the genus Fusarium;

(4) the protein according to any of the above (1) to (3), which is a D-pantolactone hydrolase, or a salt thereof, having an amino acid sequence represented by SEQ ID NO:1 or an amino acid sequence substantially equivalent thereto;

(5) the protein according to any of the above (1) to (4), which is produced by expressing an exogenous DNA sequence in procaryotic host cells;

(6) the protein according to any of the above (1) to (5), which has an amino acid sequence represented by SEQ ID NO:1 or the substantially same amino acid sequence as it has;

(7) a partial peptide, or a salt thereof, of the protein according to any of the above (1) to (6);

(8) a nucleic acid having a nucleotide sequence coding for the protein or partial peptide thereof according to any of the above (1) to (7);

(9) the nucleic acid according to the above (8), which has a nucleotide sequence having a portion corresponding to an open reading frame in the nucleotide sequence of SEQ ID NO:2 or a nucleotide sequence having an activity substantially equivalent thereto;

(10) a vector carrying the nucleic acid according to the above (8) or (9);

(11) a transformant wherein the vector according to the above (10) is harbored;

(12) a process for producing the protein or partial peptide thereof according to any of the above (1) to (7), including a D-pantolactone hydrolase or a salt thereof, which comprises:
culturing the transformant according to the above (11) in a nutrient medium suitable for growing said transformant to produce, as a recombinant protein, the protein or partial peptide thereof according to any of the above (1) to (7), including said D-pantolactone hydrolase or a salt thereof; and

(13) a process for producing D-pantolactone, which comprises:
carrying out an optical resolution of D,L-pantolactone in the presence of
(i) the protein or partial peptide thereof according to any of the above (1) to (7) or
(ii) the transformant according to the above (11).

More specifically, the present invention provides a D-pantolactone hydrolase, or a salt thereof, having an amino acid sequence of SEQ ID NO:1.

BRIEF DESCRIPTION OF DRAWINGS

FIG. 1 (SEQ ID NOS 3–22, respectively) shows the amino acid sequences obtained by sequencing of digestive peptides of D-pantolactone hydrolase.

FIG. 2 (SEQ ID NO:1) shows sites each corresponding to a digestive peptide of D-pantolactone hydrolase on the amino acid sequence for which the isolated cDNA codes.

FIG. 3 (SEQ ID NOS 23–24 and 25–26, respectively) shows the structures of primers applied in PCR wherein a genomic DNA for D-pantolactone hydrolase is used as a template.

FIG. 4 (SEQ ID NOS 27, 28 and 29, respectively) shows the structures of primers applied in PCR for the construction of a vector used for expressing recombinant D-pantolactone hydrolase.

FIG. 5 (SEQ ID NOS 1–2, respectively) shows the amino acid sequence and nucleotide sequence of D-pantolactone hydrolase.

DETAILED DESCRIPTION OF THE INVENTION

The present invention provides techniques such as cloning of a gene coding for naturally-occurring D-pantolactone hydrolase (such as natural D-pantolactone hydrolase derived from (or originating in) *Fusarium oxysporum*) or a protein having an activity substantially equivalent thereto, identification of said gene and determination of the characteristic sequence (sequencing) of said gene as well as recombination of said gene to an expression vector; production and culture/growth of host cells transformed with DNA containing a nucleotide sequence coding for said protein (transformants); production of said protein via using said host cell; and use of such proteins and host cells.

Described herein below are detailed techniques and operations according to the present invention.

The present invention also provides various means for utilizing genes coding for the above-mentioned D-pantolactone hydrolase and further provides a D-pantolactone hydrolase production system with a good efficiency and a more excellent productivity wherein said isolated D-pantolactone hydrolase gene is utilized.

The present invention relates to a protein having a naturally-occurring D-pantolactone hydrolase activity or an activity substantially equivalent thereto or a salt thereof, or a protein having a primary structural conformation substantially equivalent thereto or a salt thereof; a characteristic partial peptide of said protein or a salt thereof; a gene, such as DNA and RNA, coding for said protein or peptide; a vector or plasmid (or vehicle) containing said gene operably in a gene recombination technique; a host cell transformed with such a vector, etc.; a process for producing said protein or a salt thereof which comprises culturing said host cell; a process for synthesizing D-pantolactone which comprises an optical resolution of D,L-pantolactone with such a gene-manipulated host cell, or said recombinant protein or a salt thereof; and systems and means, such as immobilized enzymes, for producing D-pantolactone.

In the present invention, D-pantolactone hydrolase or a salt thereof which comprises, preferably, an amino acid sequence of SEQ ID NO:1 or a amino acid sequence substantially equivalent thereto is specifically illustrated but the D-pantolactone hydrolase of the present invention includes any enzyme which has a D-pantolactone hydrolyzing ability as long as it has a novel amino acid sequence. The D-pantolactone hydrolyzing ability refers to any ability which is in the same quality in view of hydrolyzing D-pantolactone. More preferably, the D-pantolactone hydrolase of the present invention includes all substances having an amino acid sequence of SEQ ID NO:1; or having a substantially equivalent amino acid sequence thereto and/or the substantially same amino acid sequence.

The D-pantolactone hydrolase gene according to the present invention may be cloned, for example, by the following processes:

It should be noted that gene recombination techniques may be conducted, for example, by the methods disclosed in T. Maniatis et al., "Molecular Cloning", 2nd Ed., Cold Spring Harbor Laboratory, Cold Spring Harbor, N. T. (1989); Nippon Seikagaku Kai (Biochemical Society of Japan) ed., "Zoku-Seikagaku Jikken Kouza 1, Idensi Kenkyuho II (Lectures on Biochemical Experiments (Second Series; 1), Methods for Gene Study II)", Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinat DNA Technique))", Tokyo Kagaku Dojin, Japan (1992); R. Wu (ed.), "Methods in Enzymology", Vol. 68, Academic Press, New York (1980); R. Wu et al. (ed.), "Methods in Enzymology", Vols. 100 and 101, Academic Press, New York (1983); R. Wu et al. (ed.). "Methods in Enzymology", Vols. 153, 154 and 155, Academic Press, New York (1987), etc. as well as by the techniques disclosed in the references cited therein, the disclosures of which are hereby incorporated by reference, or by the substantially same techniques as they disclose or modified techniques thereof. Such techniques and means may also be those which are individually modified/improved from conventional techniques depending upon the object of the present invention.

1) Cloning of Partial Genomic DNA of D-Pantolactone Hydrolase

Cultured *Fusarium oxysporum* cells are disrupted, and centrifuged to isolate chromosomal DNA, followed by decomposition and removal of RNA, in a conventional manner. DNA components are purified by removing proteins therefrom. Further information on preparation of the materials referred to in this application is disclosed, for example, in "Shokubutsu Biotechnology-Jikken Manual (Plant Biotechnology Experiment Manual)", Noson Bunkasha, page 252, the disclosures of which are hereby incorporated by reference.

As a source for DNA, any microorganism which belongs to the genus Fusarium and has an ability of producing D-pantolactone hydrolase may be suitably used. Examples of the microorganism belonging to the genus Fusarium which is applicable here are *Fusarium oxysporum* IFO 5942, *Fusarium semitectam* IFO 30200, etc.

Similarly, other microorganisms which belong to a member selected from the group consisting of the genera: Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium or Arthroderma and have the ability to produce D-pantolactone hydrolase may be used as a source for DNA. Examples of such microorganisms are *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928, *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, *Arthroderma uncinatum* IFO 7865, etc., wherein "IFO" is Zaidan-Hojin Hakko Kenkyusho (the Institute for Fermentation, Osaka; 17–85, Juso-hon-machi 2-chome, Yodogawa-ku, Osaka 532, Japan) and each number thereafter stands for the number in the Catalog issued by said IFO or the Accession Number given by IFO.

2) Preparation of Probe

Synthetic oligonucleotide primers are prepared according to information on amino acid sequences regarding the internal peptide of D-pantolactone hydrolase. For example, synthetic oligonucleotide primers can be prepared according to information on amino acid sequences regarding the internal peptide of pure D-pantolactone hydrolase obtained from the microorganism which is selected from those mentioned hereinabove and has an ability of producing D-pantolactone hydrolase. In a typical case, degenerate primers, etc. are designed and prepared based upon information on the amino acid sequence of natural D-pantolactone hydrolase fragments. Preparation of primers may be carried out by techniques which are known in the art. For example, the primers may be synthesized by means of a phosphodiester method, a phosphotriester method, a phosphoamidite method, etc. using an automatic DNA synthesizer. To be more specific, D-pantolactone hydrolase is purified from the cells obtained by culturing *Fusarium oxysporum* IFO 5942 in a nutrient medium and fragmented, if necessary, with a peptidase, etc. whereupon the information on an amino acid sequence of the internal peptide of the enzyme is collected. From the information on the amino acid sequence obtained as such, preferred synthetic oligonucleotide primers are designed and prepared. A polymerase chain reaction (PCR) is carried out using a pair of said primers wherein a genomic DNA for D-pantolactone hydrolase is used as a template. The PCR may be carried out by techniques known in the art or by methods substantially equivalent thereto or modified techniques. The reaction may be conducted by the methods disclosed, for example, in R. Saiki, et al., Science, Vol. 230, pp. 1350 (1985); R. Saiki, et al., Science, Vol. 239, pp. 487 (1988); and Henry A. Erlich, PCR Technology, Stockton Press. The reaction may also be carried out, for example, using a commercially available kit or reagent.

The resulting amplified DNA fragments are sequenced and, after confirming that they contain a sequence which is homologous to that coding for the amino acid sequence of the internal peptide of the purified enzyme, they are labeled with an isotope and are used for future experiments or the like. Sequencing of nucleotide sequences may be carried out by a dideoxy technique (such as an M13 dideoxy method), a Maxam-Gilbert method, etc. or may be carried out using a commercially available sequencing kit such as a Taq dyeprimer cycle sequencing kit or an automatic nucleotide sequencer such as a fluorescent DNA sequencer. Labeling of probes, etc. with a radioisotope, etc., may be carried out using a commercially available labeling kit such as a random primed DNA labeling kit (Boehringer Mannheim).

3) Cloning of D-Pantolactone Hydrolase cDNA a) Preparation of mRNA and Construction of cDNA Library.

Cultured *Fusarium oxysporum* cells are disrupted, extracted according to an AGPC method to isolate total RNA. Then mRNA is isolated and purified from the total RNA fraction by a suitable method such as by the use of an oligo dT cellulose column. Although, in an embodiment, mRNA may be isolated with a method known in the art or by the substantially same method as it is or modifications thereof, the isolation and purification of mRNA can be conducted by methods disclosed in, for example, T. Maniatis, et al., "Molecular Cloning", 2nd Ed., Chapter 7, Cold Spring Harbor Laboratory, Cold Spring Harbor, N. T. (1989); L. Grossman, et al. ed., "Methods in Enzymology", Vol. 12, Parts A & B, Academic Press, New York (1968); S. L. Berger et al. ed., "Methods in Enzymology", Vol. 152, p. 33 & p. 215, Academic Press, New York (1987); Biochemistry, 18, 5294–5299, 1979; etc., the disclosures of which are hereby incorporated by reference. Examples of such mRNA isolating and purifying techniques are a guanidine-cesium chloride method, a guanidine thiocyanate method, a phenol method, etc. If necessary, the resulting total RNA may be subjected to a purification process using an oligo(dT)-cellulose column, etc. to give poly(A)$^+$ mRNA. As a source for mRNA, any microorganism which belongs to the genus Fusarium and has an ability of producing D-pantolactone hydrolase may be suitably used. Examples of the microorganism belonging to the genus Fusarium which is applicable herein are *Fusarium oxysporum* IFO 5942, *Fusarium semitectam* IFO 30200, etc. Similarly, other microorganisms which belong to a member selected from the group consisting of the genera: Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium or Arthroderma and have an ability of producing D-pantolactone hydrolase may be used as a source for mRNA. Examples of such microorganisms are *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928, *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, *Arthroderma uncinatum* IFO 7865, etc.

cDNAs are prepared by using, as a template, the resulting mRNA and a reverse transcriptase, etc. The reverse transcriptase synthesis of cDNA using mRNA may be carried out by standard techniques known in the art, by the substantially same techniques or by modified techniques thereof. Detailed techniques are found in, for example, H. Land et al., "Nucleic Acids Res.", Vol. 9, 2251 (1981); U. Gubler et al., "Gene", Vol. 25, 263–269 (1983); S. L. Berger et al. ed., "Methods in Enzymology", Vol. 152, p. 307, Academic Press, New York (1987); etc., the disclosures of which are hereby incorporated by reference. The cDNA thus obtained is inserted into a commercially available phage vector or, further, subjected to a packaging by conventional techniques. Then, based upon the cDNA thus prepared, cDNA libraries can be constructed.

b) Cloning of D-Pantolactone Hydrolase cDNA.

The above recombinant phage was transfected into host cells, followed by subjecting to a plaque hybridization to select positive plaques (clones). DNA fragments from the resulting clones are sequenced. The resultant nucleotide sequences are decoded and analyzed in view of an encoded amino acid sequence. As a result of such analyses and investigations, it is confirmed that the target D-pantolactone hydrolase gene is cloned.

Besides the technique using a phage vector, transformations of host cells including *Escherichia coli* may be conducted according to techniques known in the art, such as a calcium technique and a rubidium/calcium technique, or the substantially same methods (D. Hanahan, J. Mol. Biol., Vol. 166, p. 557 (1983), etc.).

PCR may be conducted using the prepared cDNA as a template. In an embodiment, the primer obtained in the above 2) can be used.

With respect to a plasmid into which the D-pantolactone hydrolase gene is incorporated, any plasmid may be used as long as said DNA can be expressed in host cells conventionally used in gene engineering techniques (such as procaryotic host cells including *Escherichia coli, Bacillus subtilis*, etc. and eucaryotic host cells including yeasts). In such a sequence of the plasmid, it is possible, for example, to incorporate codons suitable for expressing the cloned DNA in selected host cells or to construct restriction enzyme sites. It is also possible to contain control sequences, promotion sequences, etc. for facilitating the expression of the aimed gene; linkers, adaptors, etc. useful for ligating the aimed gene; sequences useful in controlling resistance to antibiotics or in controlling metabolism or in selection; and the like.

Preferably, suitable promoters may be used. For example, such promoters may include tryptophan (trp) promoter, lactose (lac) promoter, tryptophan-lactose (tac) promoter, lipoprotein (lpp) promoter, λ phage $P_L$ promoter, etc. in the case of plasmids where *Escherichia coli* is used as a host; and GAL1, GAL10 promoters, etc. in the case of plasmids where yeast is used as a host.

Examples of the plasmid suitable for host *Escherichia coli* are pBR322, pUC18, pUC19, pUC118, pUC119, pSP64, pSP65, pTZ-18R/-18U, pTZ-19R/-19U, pGEM-3, pGEM-4, pGEM-3Z, pGEM-4Z, pGEM-5Zf(-), pBluescript KS™ (Stratagene), etc. Examples of the plasmid vector suitable for expression in *Escherichia coli* are pAS, pKK223 (Pharmacia), pMC1403, pMC931, pKC30, etc. Examples of the plasmid for host yeasts are YIp vector, YEp vector, YRp vector, YCp vector, etc., including pGPD-2, etc. *Escherichia coli* host cells may include those derived from *Escherichia coli* K12 strains, such as NM533, XL1-Blue, C600, DH1, HB101 and JM109.

In the gene engineering techniques of the present invention, it is possible to use various restriction enzymes, reverse transcriptases, enzymes for DNA modification and decomposition, used for modifying or converting a DNA fragment to a structure suitable for cloning, DNA polymerases, terminal nucleotidyl transferases, DNA ligases; etc., which are known or common in the art. Examples of the restriction enzyme are those disclosed in R. J. Roberts, "Nucleic Acids Res.", Vol. 13, r165 (1985); S. Linn et al. ed., "Nucleases", p. 109, Cold Spring Harbor Lab., Cold Spring Harbor, N.Y., 1982; etc. Examples of the reverse transferase are those derived from mouse Moloney leukemia virus (MMLV), from avian myeloblastosis virus (AMV), etc. Particularly, RNase H-deficient reverse transferase or the like is preferably used. Examples of the DNA polymerase are *Escherichia coli* DNA polymerase, Klenow fragment which is a derivative of *E. coli* DNA polymerase, *E. coli* phage T4 DNA polymerase, *E. coli* phage T7 DNA polymerase, thermoduric bacteria DNA polymerase, etc.

The terminal nucleotidyl transferase includes TdTase capable of adding a dideoxynucleotide (dNMP) to a 3'-OH terminal, as disclosed in R. Wu et al. ed., "Methods in Enzymology", Vol. 100, p. 96, Academic Press, New York (1983). The enzyme for modifying and decomposing DNA includes exonuclease, endonuclease, etc. Examples of such enzymes are snake toxin phosphodiesterase, spleen phosphodiesterase, *E. coli* DNA exonuclease I, *E. coli* DNA exonuclease III, *E. coli* DNA exonuclease VII, λ exonuclease, DNase I, nuclease S1, Micrococcus nuclease, etc. Examples of the DNA ligase are *E. coli* DNA ligase, T4 DNA ligase, etc.

The vector (or vehicle) which is suitable for cloning DNA genes and constructing DNA libraries includes plasmid, λ phage, cosmid, P1 phage, F factor, YAC, etc. Preferred examples of such vectors are vectors derived from λ phage, such as Charon 4A, Charon 21A, λ gt10, λ gt11, λ DASHII, λ FIXII, λ EMBL3 and λ ZAPII™ (Stratagene), etc.

In addition, based upon the gene nucleotide sequence encoding the D-pantolactone hydrolase of the present invention, methods and means conventionally used in gene engineering techniques enable us to manufacture proteins, such as variants and mutants, wherein a modification is introduced into the amino acid sequence of the D-pantolactone hydrolase in such a manner that one or more amino acid(s) is/are substituted, deleted, inserted, translocated or added. Examples of the methods and means for such a variation, substitution and modification are those disclosed in Nippon Seikagaku Kai (Biochemical Society of Japan) ed., "Zoku-Seikagaku Jikken Kouza 1, Idensi Kenkyuho II (Lectures on Biochemical Experiments (Second Series; 1), Methods for Gene Study II)", p.105 (Susumu Hirose), Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinat DNA Technique))", p. 233 (Susumu Hirose), Tokyo Kagaku Dojin, Japan (1992); R. Wu, L. Grossman, ed., "Methods in Enzymology", Vol. 154, p. 350 and p. 367, Academic Press, New York (1987); R. Wu, L. Grossman, ed., "Methods in Enzymology", Vol. 100, p.457 and p. 468, Academic Press, New York (1983); J. A. Wells et al., "Gene", Vol. 34, p. 315 (1985); T. Grundstroem et al., "Nucleic Acids Res.", Vol. 13, p. 3305 (1985); J. Taylor et al., "Nucleic Acids Res.", Vol. 13, p. 8765 (1985); R. Wu, ed., "Methods in Enzymology", Vol. 155, p. 568, Academic Press, New York (1987); A. R. Oliphant et al., "Gene", Vol. 44, p.177 (1986); etc., the disclosures of which are hereby incorporated by reference. Examples of such methods and means are techniques utilizing synthetic oligonucleotides for introducing a mutation or variation into a specific site (site-directed mutagenesis techniques), Kunkel techniques, dNTP[α S] techniques (Eckstein method), techniques using sulfurous acid (or bisulfite), nitrous acid (or nitrite), etc. for introducing a mutation or variation into a specific domain or area, etc.

Moreover, the resulting protein according to the present invention may be subjected to chemical techniques whereby an amino acid residue(s) contained therein is(are) modified or may be made into its(their) derivative(s) by subjecting to a partial decomposition or a modification using an enzyme such as peptidase (for example, pepsin, chymotrypsin, papain, bromelain, endopeptidase, exopeptidase, etc.). It is also possible to express, as fusion proteins, the recombinant proteins of the present invention on the manufacture by means of gene recombinant techniques and then to convert/process the fusion proteins in vivo or in vitro to products having a biological activity substantially equivalent to a natural D-pantolactone hydrolase. A fusion production conventionally used in gene engineering techniques may be used as well. Such a fusion protein may be purified by means of an affinity chromatography, etc. utilizing its fusion part. Modifications, alterations, etc. of protein structures are found, for example, in Nippon Seikagaku Kai (Biochemical Society of Japan) ed., "Shin-Seikagaku Jikken Kouza 1, Tanpakushitsu VII, Tanpakushitsu Kogaku (New Lectures on Biochemical Experiments 1, Protein VII, Protein Engineering)", Tokyo Kagaku Dojin, Japan (1993), the disclosures of which are hereby incorporated by reference. Such modifications, alterations, etc. may be conducted according to techniques disclosed therein, techniques disclosed in references cited therein, and those substantially similar thereto.

Thus, the products according to the present invention may include either proteins wherein one or more amino acid residue(s) is/are different from that/those of the natural one in terms of identity or proteins wherein one or more amino acid residue(s) is/are shifted from the position(s) of the natural one. The products according to the present invention may include deletion analogs wherein one or more amino acid residue(s) specified for the natural D-pantolactone hydrolase is/are deficient therefrom (for example, 1 to 80, preferably 1 to 60, more preferably 1 to 40, still more preferably 1 to 20 and particularly preferably 1 to 10 amino acid residue(s) specified for the natural D-pantolactone hydrolase is/are deficient therefrom); substitution analogs, wherein one or more amino acid residue(s) specified for the natural D-pantolactone hydrolase is/are replaced with other residue(s) (for example 1 to 80, preferably 1 to 60, more preferably 1 to 40, still more preferably 1 to 20 and particularly preferably 1 to 10 amino acid residue(s) specified for the natural D-pantolactone hydrolase is/are replaced with other residue(s)); and addition analogs, wherein one or more amino acid residue(s) is/are added to the sequence specified for the natural D-pantolactone hydrolase (for example 1 to 80, preferably 1 to 60, more preferably 1 to 40, still more preferably 1 to 20 and particularly preferably 1 to 10 amino acid residue(s) is/are added to the amino acid sequence specified for the natural D-pantolactone hydrolase. The products may include proteins wherein a domain structure characteristic to the natural D-pantolactone hydrolase is contained or retained. Further, the products may include proteins having the same quality in view of D-pantolactone hydrolase activity as the natural D-pantolactone hydrolase.

The products of the present invention may include all of the variants and analogs as mentioned herein above, as long as they have the domain structure which is characteristic to the naturally-occurring D-pantolactone hydrolase. It is also believed that the products of the present invention may include all proteins having a primary structural conformation substantially equivalent to that of the naturally-occurring D-pantolactone hydrolase according to the present invention and those having a portion of the primary structural conformation of naturally-occurring D-pantolactone hydrolase according to the present invention. It is further believed that the products of the present invention may include proteins sharing all or part of the biological properties of naturally-occurring D-pantolactone hydrolase or having a biological activity substantially equivalent to that of the natural D-pantolactone hydrolase. Furthermore, the product of the present invention may include one of the variants which naturally occur. The D-pantolactone hydrolase products of the present invention can be separated, isolated or/and purified as illustrated hereinafter.

Further, the products according to the present invention may include DNA sequences coding for the above-mentioned polypeptide and DNA sequences encoding D-pantolactone hydrolase polypeptides (including analogs and derivatives thereof) having all or part of the natural characteristics of the naturally-occurring D-pantolactone hydrolase. Said D-pantolactone hydrolase nucleotide sequences may also be modified (such as inserted, added, deleted and substituted). Thus, the products according to the present invention may include such modified nucleotide sequences as well.

Since the DNA sequences of the present invention provide information on the amino acid sequence of D-pantolactone hydrolase protein which has heretofore been unavailable, utilization of such information is within the scope of the present invention as well. Such utilization may include designing of probes for isolation and/or detection of genomic DNA and cDNA coding for D-pantolactone hydrolase or proteins related thereto, of microorganisms, or particularly preferably microorganisms having an ability of producing D-pantolactone hydrolase, such as those belonging to a member selected from the group consisting of the genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma with an ability of producing D-pantolactone hydrolase.

The DNA sequences of the present invention are valuable, for example, as probes for isolation and/or detection of genomic DNA and cDNA coding for D-pantolactone hydrolase or proteins related thereto, of microorganisms having an ability of producing D-pantolactone hydrolase, or particularly preferably microorganisms belonging to the above-mentioned genus, including the Fusarium, etc. Isolation of the gene may be carried out by utilizing PCR techniques or RT-PCR techniques (PCR using a reverse transcriptase (RT)). D-Pantolactone hydrolase DNA and its related DNA may be utilized for isolation, detection, etc. of genes related to D-pantolactone hydrolase by means of PCR techniques, RT-PCR techniques or other methods, using a DNA primer obtained by a chemical synthesis as a result of selecting a characteristic domain (or portion) based upon a putative amino acid sequence derived from the cloned and sequenced D-pantolactone hydrolase cDNA sequence and of designing the DNA primer relied on the selected domain (or portion).

As mentioned hereinabove, the present invention provides a process for producing the aimed D-pantolactone hydrolase which comprises importing a recombinant D-pantolactone hydrolase DNA molecule and/or gene into hosts followed by expressing the D-pantolactone hydrolase therein. Thus, in accordance with the present invention, recombinants (transformants) or transfectants which are endowed with the capacity to substantially express the same; and use thereof are provided.

Another aspect of the present invention also relates to nucleic acids, such as DNA and RNA, which enable the expression in eucaryotic or procaryotic host cells, such as *Escherichia coli* host cells of (1) proteins or salts thereof having a D-pantolactone hydrolase activity;

(2) proteins or salts thereof characterized in having a substantially equivalent activity thereto; or (3) polypeptides having all or at least a part of a D-pantolactone hydrolase protein or a salt thereof (more preferably D-pantolactone hydrolase protein originating in *Fusarium oxysporum*) and having the substantially equivalent activity or the substantially same primary structural conformation.

In addition, such a nucleic acid, particularly DNA, may be:

(a) a sequence capable of encoding the amino acid sequence of SEQ ID NO:1 or a sequence complementary thereto;

(b) a sequence capable of hybridizing with said DNA sequence (a) or a fragment thereof; and (c) a sequence having a degenerate code capable of hybridizing with the sequence (a) or (b).

The characteristics of the present invention reside in eucaryotic or procaryotic host cells, such as *Escherichia coli* host cells, transformed or transfected with such a nucleic acid, which are endowed with the capacity to express said polypeptide of the present invention.

It may also be possible in accordance with the present invention to obtain a microorganism in which its ability to produce D-pantolactone hydrolase is modified by introducing (i) DNA coding for a protein having a D-pantolactone hydrolase activity or a protein having the substantially equivalent activity thereto or (ii) DNA, such as vector, containing said DNA into said microorganism in an expressible manner. Such microorganisms possessing the ability to produce D-pantolactone hydrolase may include microorganisms belonging to a member selected from the group consisting of the genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma. Examples of such microorganisms are *Fusarium oxysporum* IFO 5942, *Fusarium semitectam* IFO 30200, *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928,; *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, *Arthroderma uncinatum* IFO 7865, etc.

Transformation may include techniques in which protoplast cells prepared by the use of a suitable cell wall lytic enzyme are contacted with DNA in the presence of calcium chloride, polyethylene glycol, etc.; electroporation techniques (see: for example, E. Neumann et al., EMBO J, Vol. 1, pp. 841 (1982), etc.); microinjection techniques; shot gun methods for shooting a gene with a gun; etc.

The enzymes can be isolated and prepared by purifying techniques from various materials, such as produced enzyme materials including cell growth culture medium, disrupted cultured cells, transformed cells, etc. The purification may include methods known in the art, including salting out such as precipitation with ammonium sulfate; gel filtration using Sephadex or the like; ion exchange chromatography technique using, for example, a carrier having a diethylaminoethyl group or a carboxymethyl group; hydrophobic chromatography technique using, for example, a carrier having hydrophobic groups including a butyl group, an octyl group, a phenyl group, etc.; pigment gel chromatography technique; electrophoresis technique; dialysis; ultrafiltration; affinity chromatography technique; high performance liquid chromatography technique; etc.

When the enzyme is obtained as an inclusion body, it may be subjected to a solubilizing treatment using, for example, a denaturing agent, such as guanidine hydrochloride and urea, and, if necessary, in the presence of a reducing agent, such as 2-mercaptoethanol and dithiothreitol, whereupon an activated form of the enzyme is produced.

For enzyme materials, enzyme-producing cells per se may be used instead. Immobilized enzymes may include products prepared by immobilizing the enzyme or enzyme-producing cells according to techniques known in the art. The immobilization can be conducted by carrier bonding techniques, such as a covalent method and an adsorption method, a cross-linking method, an encapsulation, etc.: The immobilization can also be conducted using a condensing agent such as glutaraldehyde, hexamethylene diisocyanate and hexamethylene diisothiocyanate if necessary. In addition, monomer techniques in which monomers are gelled in a polymerization, prepolymer techniques in which molecules having bigger size than conventional monomers are polymerized, polymer techniques in which polymers are gelled, etc. may be exemplified. It may include an immobilization using polyacrylamide, an immobilization using natural polymers such as alginic acid, collagen, gelatin, agar and κ-carrageenan, an immobilization using synthetic polymers such as photosetting resins and urethane polymers, etc. It may be possible to carry out the optical resolution of lactone compounds by an enzymatic asymmetric hydrolysis utilizing a lactone hydrolase (such as a D-pantolactone hydrolysis using a culture of microorganisms and enzymes), as well as treatment of products obtained thereby in the same manner as disclosed in Unexamined Japanese Patent Publication (KOKAI TOKKYO) Nos. Hei 3-65,198 and Hei 4-144,681.

For example, the transformed microorganisms (transformants) thus obtained are subjected to shaking culture in a liquid medium. The resulting cultured cells are harvested, to which an aqueous solution of D,L-pantolactone (concentrations: 2 to 60%) is added. The mixture is made to react at 10 to 40° C. for from several hours to one day while adjusting the pH to from 6 to 8. After completion of the reaction, the cells are separated and the unreacted L-pantolactone in the reaction solution is separated by extracting with an organic solvent (preferably an ester such as ethyl acetate, an aromatic hydrocarbon such as benzene or a halogenated hydrocarbon such as chloroform). D-Pantoic acid remaining in the aqueous layer is heated under an acidic condition with hydrochloric acid to conduct a lactonation followed by extracting with the above-mentioned organic solvent whereupon the resulting D-pantolactone is obtained. As such, processed cells (dried cells, immobilized cells, etc.) of the transformed microorganisms or enzymes and immobilized enzymes obtained from the transformed cells can be used in the same manner as well.

As a result of utilization of various embodiments of the present invention as mentioned hereinabove, it is now possible to provide various technical means, such as means valuable or useful for the synthetic studies concerning an optical resolution of lactone compounds by an enzymatic asymmetric hydrolysis utilizing a lactone hydrolase (for example, D-pantolactone hydrolase) as well as means applicable to other uses. The present invention will be more specifically illustrated by way of the following examples although it is to be understood that the present invention is not limited to such examples but various embodiments within the spirit of this specification are possible.

Incidentally, when nucleotides (bases) and amino acids are indicated by abbreviations in the specification and in the drawings, they depend upon an "IUPAC-IUB Commission on Biochemical Nomenclature" or upon the meanings of the terms which are commonly used in the art. When optical isomers are present in amino acids, an L-isomer is referred to unless otherwise specified.

The transformant *Escherichia coli*, designated JM109 (EJM-ESE-1) having a recombinant vector (PFLC40E) into which the enzyme D-pantolactone hydrolase gene is integrated and obtained in Example 1 mentioned herein below has been deposited as from Aug. 30, 1995 (original deposit date) with the National Institute of Bioscience and Human Technology (NIBH), Agency of Industrial Science and Technology, Ministry of International Trade and Industry, Japan, located at 1–3, Higashi 1-chome, Tsukuba-shi, IBARAKI (Zip Code: 305), JAPAN and has been assigned the Accession Number FERM P-15141. The original deposit of the transformant *E. coli* JM109 (EJM-ESE-1) has been transferred to one under the Budapest Treaty by a request dated Aug. 28, 1996 and is on deposit with the Accession Number FERM BP-5638 under the terms of the Budapest Treaty at NIBH.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1
1) Amino Acid Sequencing of Purified Enzyme

A sample of freeze-dried D-pantolactone hydrolase (14.3 nmol; subunit molecular weight: 60,000) prepared according to Example 1 in Unexamined Japanese Patent Publication (KOKAI TOKKYO) No., Hei 4-144,681 was dissolved in 44 $\mu$l of 50 mM Tris-HCl (pH: 9.0) containing 8M urea and was denatured at 37° C. for 1 hr. To this solution was added 44 $\mu$l of 50 mM Tris-HCl (pH: 9.0) whereupon the urea concentration was made 4M. Then 12 $\mu$l (0.144 nmol; E/S=1/100) of 12 nmol/ml of lysyl endopeptidase (Wako Pure Chemicals, Japan; was added thereto and a digestion was carried out at 30° C. for 12 hrs. The resulting digested peptide was collected by means of a reversed phase column (Nakarai Tesuku, Japan) and analysis of the amino acid sequence was carried out using a 477A Protein Sequencer (ABI, USA).

Collecting Conditions
Column: Cosmosil 5C18-AR (4.6×250 mm)
Flow Rate: 1 ml/min.
Temperature: 35° C.
Detecting Wave Length: 210 nm
Eluting Solution:
  A, 0.1% TFA (TFA: trifluoroacetic acid)
  B, 0.1% TFA/80% CH$_3$CN
Eluting Conditions: Gradient elution of A→B (15%/min.)
Results of the amino acid sequencing was as shown in FIGS. 1 and 2.

2) Preparation of Genomic DNA.
a) Process for the Extraction of Genomic D-Pantolactone Hydrolase DNA Cultured cells at an anaphase of a logarithmic growth phase were harvested by means of a filtration in vacuo. The cells were placed in liquid nitrogen and finely disrupted using a Waring Blender. The cell mixtures which were made fine to some extent were transferred to a mortar and ground together with the addition of liquid nitrogen. This product was suspended in a 2×CTAB solution (2% CTAB (CTAB: cetyl trimethylammonium bromide; Sigma, USA), 0.1M Tris-HCl (pH 8.0), 1.4M NaCl and 1% PVP (PVP: polyvinylpyrrolidone; Sigma, USA)) kept at 70° C. and incubated at 65° C. for 3–4 hours. The supernatant liquid obtained by centrifugation was successively treated with phenol, phenol/chloroform and chloroform and the resultant solution was then treated with the same volume of isopropanol to precipitate DNA. This DNA paste was washed with 70% ethanol, air-dried and dissolved in a TE buffer (10 mM Tris and 1 mM EDTA;,pH 7.8). RNA was decomposed with ribonuclease A and ribonuclease T1. Then the DNA product was successively treated with phenol, phenol/chloroform and chloroform to remove the protein therefrom. The resultant product was treated with the same volume of isopropanol to precipitate DNA. This DNA was washed with 70% ethanol, air-dried and dissolved in a TE buffer to afford a genome sample.

b) Amplification of D-Pantolactone Hydrolase Gene

Based upon the information on amino acid sequences (FIGS. 1 and 2) of D-pantolactone hydrolase internal peptides, a sense primer corresponding to a sense strand coding for the N-terminal amino acid sequence and an antisense primer corresponding to an antisense strand for the internal peptide sequence were synthesized (FIG. 3).

PCR was carried out under the following conditions using, as a template, a genomic DNA sample of D-pantolactone hydrolase:

The PCR was conducted by the techniques mentioned in the art, for example, in R. Saiki, et al., Science, Vol. 230, pp. 1350 (1985); R. Saiki, et al., Science, Vol. 239, pp. 487 (1988); PCR Technology, Stockton Press (1989); etc.

As a result of the PCR, amplified DNA fragments with about 1 kb were obtained.

| PCR Conditions | |
| --- | --- |
| Genomic DNA: | 2.5 µg |
| Sense Primer: | 250 pmol (cf. FIG. 3) |
| Antisense Primer: | 250 pmol (cf. FIG. 3) |
| dNTP (2 mM): | 5 µl |
| Tth Polymerase Buffer (×10): | 5 µl |
| Tth DNA Polymerase (Toyobo, Japan): | 3 units |
| H$_2$O: | |
| Total | 50 µl |

The cycle for amplification including 92° C. for 1 min., 55° C. for 1 min. and 73° C. for 3 min. was repeated 30 times.

The resulting amplified DNA fragments were subjected a sequencing and the disclosed DNA sequence was decoded to an amino acid sequence whereby a portion corresponding to the partial amino acid sequence of the D-pantolactone hydrolase internal peptide was found among the decoded amino acid sequences.

3) Preparation of cDNA a) Preparation of mRNA

Cultured cells were harvested at a prophase of the logarithmic growth phase, immediately frozen with liquid nitrogen, disrupted and subjected to an AGPC (Acid Guanidinium Thiocyanate Phenol Chloroform Method; see, for example, Jikken Igaku, Vol. 15, p. 99 (1991)) to extract total RNA. The resulting total RNA was subjected to an oligo dT-cellulose column (Pharmacia) for purification to afford a mRNA fraction.

b) Preparation of cDNA Library

The resulting mRNA was used as a template for synthesizing cDNA by a cDNA rapido adaptor ligation module (cDNA synthesis module RPN 1256, 1994; Amersham International PLC) and the cDNA was used for construction of cDNA Libraries.

c) Cloning of D-Pantolactone Hydrolase cDNA

The cDNA libraries were infected to host *Escherichia coli* cells and positive plaques were selected by means of a plaque hybridization. In the plaque hybridization, probes used for selection were prepared by using about 1 kb fragments containing *Fusarium oxysporum* D-pantolactone hydrolase gene and by labeling the about 1 kb fragments according to a multiprime method. The resulting positive clone was sequenced and the disclosed DNA sequence was decoded to an amino acid sequence whereby it was found that the full length of the above D-pantolactone hydrolase gene was successfully cloned.

As such, the isolated and sequenced DNA has a nucleotide sequence of SEQ ID NO:2. The sequence showing a homology with the amino acid sequence represented by SEQ ID NO:1 encoded by this nucleotide sequence is not present in the Protein Sequence Data Bank of NBRF (National Biomedical Research Foundation). Thus, the DNA having this nucleotide sequence has been found to be entirely novel.

It was found that, in the cDNA where the nucleotides were sequenced, a part of the N-terminal region was lacked and there was no initiation codon therein. Therefore, an initiation codon was artificially incorporated into the cDNA by a PCR technique to construct a vector for expressing the gene (PFLC40E).

Sense and antisense oligonucleotide primers having the restriction enzyme sites as shown in FIG. 4 were synthesized. PCR was carried out utilizing those primers under the following conditions:

The PCR was conducted by the techniques mentioned in the art, for example, in R. Saiki, et al., Science Vol. 230, pp. 1350 (1985); R. Saiki, et al., Science, Vol. 239, pp. 487 (1988); and PCR Technology, Stockton Press (1989).

| PCR Conditions | |
| --- | --- |
| Total DNA (cDNA): | 10 µg |
| Sense Primer: | 0.1 nmol (cf. FIG. 4) |
| Antisense Primer: | 0.1 nmol (cf. FIG. 4) |
| dNTP (2 mM): | 10 µl |
| Tth Polymerase Buffer (×10): | 10 µl |
| Tth DNA Polymerase: | 4 units |
| H$_2$O: | |
| Total | 100 µl |

The cycle for amplification including 94° C. for 1 min., 55° C. for 1 min. and 75° C. for 3 min. was repeated 30 times.

The PCR products prepared as such had each restriction enzyme EcoRI and XbaI sites at their both terminals. Therefore, each of them was treated with EcoRI (Takara Shuzo, Japan) and XbaI (Takara Shuzo, Japan) followed by a ligation with pUC18 (Takara Ligation Kit; Takara Shuzo, Japan) whereby the expression vector (PFLC40E) was constructed.

Then said vector was transfected into *E. coli* JM 109 competent cells according to a technique as mentioned in "Molecular Cloning", Second Edition, 1989, edited by J. Sambrook, et al., Cold Spring Harbor Laboratory Press, to transform host cells. The target transformants were selected on a 2×YT medium (1.5% tryptone, 1% yeast extract and 0.5% NaCl) containing 50 mg/liter ampicillin. The transformation was done according to a calcium chloride technique.

The transformant *E. coli* prepared as such was precultured in a test tube containing 10 ml of the above-mentioned 2×YT medium containing 50 mg/liter ampicillin and then the resulting precultured solution (100 µl in total) was used as seed cells for checking culture time, culture temperature and periods for adding isopropyl-β-thiogalacto-pyranoside (IPTG) in 100 ml of main culture broths having the same composition as the preculture broth.

Results of the culture is shown in Table 1.

After the cultivation, the resulting harvested cells were disrupted by ultra-sonication and centrifuged to afford a supernatant. The resultant supernatant was measured in view of D-pantolactone hydrolase activity.

The specific activity was 2.25 U/mg at an optimal condition. Enzymatic activities of the recombinant proteins were assayed in view of D-pantolactone hydrolase under the following conditions:

The enzymatic activity capable of hydrolyzing 1 µmol of D-pantolactone per minute was defined as one unit (U). To 200 µl of 10% D-pantolactone solution in 0.5M PIPES buffer (pH 7.0) was added 50 μl of an enzyme solution and the mixture was made to react at 30° C. for 120 minutes followed by adding 250 μl of 2 mM EDTA in methanol to quench the reaction. After completion of the reaction, the liquid reaction mixture was subjected to an HPLC (Nucleosil $5C_{18}$4.6×150 mm; eluent: 10% methanol; flow rate: 1 ml/minute; detection wavelength: 230 nm) to determine the % hydrolysis. For example, where the % hydrolysis is 1%, the enzymatic activity/ml of the enzyme solution corresponds to $1.6×10^{-2}$ U/ml.

The transformant E. coli JM109, transformed with PFLC40E, was cultured in a 2×YT medium. IPTG was added thereto to make its final concentration 2 mM.

TABLE 1

| Time for Supply-ing IPTG (hr) | Culturing Time (hr) | Culturing Temperature (° C.) | Specific Activity (units/mg) |
|---|---|---|---|
| 0 (a) | 6 | 28 | 0.86 |
| 0 (a) | 12 | 28 | 1.94 |
| 4 (b) | 7 | 28 | 1.33 |
| 4 (b) | 12 | 28 | 2.25 |
| 0 (a) | 6 | 37 | 1.05 |
| 0 (a) | 12 | 37 | 1.73 |
| 4 (b) | 7 | 37 | 1.31 |
| 4 (b) | 12 | 37 | 1.67 |

(a): IPTG was added to the 2 × YT medium together with the initiation of the culture.
(b): IPTG was added to the 2 × YT medium after four hours from the initiation of the culture.

As a result of an SDS-PAGE, a deep band with an expected molecular weight was detected for an insoluble fraction of the centrifuged precipitate. Therefore, the band was subjected to a blotting and the sample was investigated in view of an N-terminal amino acid sequence by an Edman degradation technique whereby its N-terminal amino acid sequence was found to be identical with that of D-pantolactone hydrolase.

Accordingly, it is likely that, although the recombinant D-pantolactone hydrolase was in part expressed as a soluble form in this E. coli expression system for expressing the D-pantolactone hydrolase cDNA, most of the recombinant D-pantolactone hydrolase is expressed as an inclusion body.

The transformant Escherichia coli, designated JM109 (EJM-ESE-1), having a recombinant vector (PFLC40E) into which the above-mentioned enzyme D-pantolactone hydrolase gene is integrated has been deposited and stored with the National Institute of Bioscience and Human Technology (NIBH), Agency of Industrial Science and Technology, Ministry of International Trade and Industry, Japan, located at 1–3, Higashi 1-chome, Tsukuba-shi, IBARAKI (Zip Code: 305), JAPAN. The transformant E. coli JM109 (EJM-ESE-1) has been assigned the Accession Number FERM BP-5638 by NIBH. A request for transferring the original deposit (Accession Number FERM P-15141 deposited on Aug. 30, 1995) to one under the Budapest Treaty was submitted on Aug. 28, 1996.

INDUSTRIAL APPLICABILITY

The present invention discloses gene structures coding for naturally-occurring D-pantolactone hydrolase (such as natural D-pantolactone hydrolase originating in Fusarium oxysporum) or for proteins having a substantially equivalent activity thereto. Thus, significant developments can be expected in applications, including uses of host cells which are transformed with DNA containing the nucleotide sequence coding for said protein, processes for the preparation of said protein using said host cells and manufacturing processes for producing D-pantolactone using such proteins and host cells. In addition, it is possible to afford a significant increase in the enzymatic activity by modification of the D-pantolactone hydrolase per se.

What is claimed is:

1. An isolated recombinant protein set forth in SEQ ID NO:1 and having D-pantolactone hydrolase activity, or a salt thereof, wherein said protein is non-glycosylated and originated from an eukaryotic microorganism having an ability to produce D-pantolactone hydrolase activity, and wherein said protein is expressed in host cells having introduced thereinto a DNA molecule encoding said protein.

2. The protein according to claim 1, which is produced by expressing an exogenous DNA sequence in procaryotic host cells.

* * * * *